United States Patent
Wagner

(10) Patent No.: US 9,291,605 B2
(45) Date of Patent: Mar. 22, 2016

(54) VALVE FOR USE IN HIGH-PERFORMANCE LIQUID CHROMATOGRAPHY HAVING A SPHERICAL SEAT WITH BEVELED OUTER FACES

(75) Inventor: Joachim-Richard Wagner, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 304 days.

(21) Appl. No.: 12/909,869

(22) Filed: Oct. 22, 2010

(65) Prior Publication Data

US 2011/0094954 A1   Apr. 28, 2011

(30) Foreign Application Priority Data

Oct. 26, 2009  (DE) .......................... 10 2009 045 987
Oct. 7, 2010   (DE) .......................... 10 2010 042 107

(51) Int. Cl.
*G01N 30/36*   (2006.01)
*F16K 1/42*    (2006.01)
*F16K 25/00*   (2006.01)
*G01N 30/32*   (2006.01)

(52) U.S. Cl.
CPC  *G01N 30/36* (2013.01); *F16K 1/42* (2013.01); *F16K 25/005* (2013.01); *G01N 2030/328* (2013.01)

(58) Field of Classification Search
CPC ......... F16K 1/42; F16K 25/005; G01N 30/36; G01N 2030/328
USPC ............................... 210/656, 198.2; 251/318
See application file for complete search history.

(56) References Cited

U.S. PATENT DOCUMENTS

| | | | |
|---|---|---|---|
| 4,456,440 A | 6/1984 | Korner et al. | |
| 4,883,409 A | 11/1989 | Strohmeier et al. | |
| 4,945,945 A * | 8/1990 | Schmid ........................ | 137/512 |
| 4,974,628 A | 12/1990 | Tepermeister et al. | |
| 2009/0076631 A1 | 3/2009 | Witt et al. | |
| 2009/0104083 A1* | 4/2009 | Aso .............................. | 422/103 |

FOREIGN PATENT DOCUMENTS

| | | |
|---|---|---|
| CN | 101418868 A | 4/2009 |
| DE | 3111614 A1 | 7/1982 |
| DE | 202006018959 | 2/2007 |
| DE | 102009001756 A1 | 7/2009 |
| EP | 0309596 A1 | 4/1989 |
| JP | 2000283309 A1 | 10/2000 |
| JP | 2005133850 A | 5/2005 |

(Continued)

OTHER PUBLICATIONS

PTO Translation No. 13-1097 of Japan Patent No. 2005133850.*

(Continued)

*Primary Examiner* — Ernest G Therkorn

(57) ABSTRACT

A valve for use in high-performance liquid chromatography has a spherical seat and a ball that, when it abuts against the seat, constrains a fluid from flowing through the valve and is capable of moving axially in order to allow the fluid to flow through the valve. The spherical seat has beveled outer faces in order that a force acting on the valve along the axial direction will generate a force acting on the ball. The inclination of the beveled outer face is such that a force acting on the ball counteracts a force exerted on the spherical seat by the ball and essentially compensates it.

12 Claims, 4 Drawing Sheets

(56) References Cited

FOREIGN PATENT DOCUMENTS

| | | | |
|---|---|---|---|
| JP | 2005133850 | A1 | 5/2005 |
| JP | 2006214539 | A1 | 8/2006 |

OTHER PUBLICATIONS

PTO Translation No. 13-1096 of Japan Patent No. 2000283309.*
PTO Translation No. 13-1095 of Japan Patent No. 2006214539.*
Office Action mailed Jul. 16, 2014 for Chinese Patent Application No. 201010531385.6.
Office Action mailed Dec. 18, 2013 for Chinese Patent Application No. 201010531385.6.
Office Action mailed Mar. 23, 2015 in German Patent Application No. 102010042107.3 (Unofficial/Non-certified translation provided by foreign agent included).
Machine translation of DE202006018959, Feb. 22, 2007.
Office Action mailed Jan. 22, 2015 in Chinese Patent Application No. 201010531385.6 (Unofficial/non-certified translation provided by foreign agent included).
Office Action mailed Oct. 4, 2015 in Chinese Patent Application No. 201010531385.6 (Unofficial/non-certified translation provided by foreign agent included).

* cited by examiner

VALVE FOR USE IN HIGH-PERFORMANCE LIQUID CHROMATOGRAPHY HAVING A SPHERICAL SEAT WITH BEVELED OUTER FACES

BACKGROUND

The present invention concerns a valve for use in high-performance liquid chromatography having a ball and a stricture that may be closed by the ball such that a fluid will be constrained from flowing through the valve.

In high-performance liquid chromatography (HPLC), a liquid must be propelled at typically very stringently controlled flow rates varying from, e.g., nanoliters/min. to milliliters/min., and high pressures typically falling within the range 20-100 MPa (200-1,000 bar) and beyond, and currently extending up to around 200 MPa (2,000 bar), where the compressibility of the liquid involved becomes evident. Liquid separation in an HPLC system involves forcing a mobile phase that, during operation, comprises a sample liquid containing components that are to be separated, through a stationary phase, such as a chromatographic column, in order to separate the various components of the sample liquid.

A serial arrangement of a pair of pumps for continuously propelling a liquid into an HPLC system is known from EP 0309596 A1. An outlet valve is situated between the primary pump and secondary pump in order to provide both that the primary pump will be unable to propel liquid into the system until the system pressure has been reached and that the secondary pump will pump liquid into the system, but not back into the primary pump.

Valves, such as outlet and/or inlet valves, are typically configured as passive check valves, where a ball is pressed against the spherical seat by the system pressure, i.e., by the pressure dropping across the ball, in order to constrain a fluid from flowing through the valve, where the ball is capable of moving in the axial direction and being lifted off the spherical seat in order to allow the fluid to flow through the valve. Active valves may also be similarly configured and employed as check valves.

Check valves are sufficiently well known from the state of the art and described in, among others, U.S. Pat. No. 4,945,945 A, U.S. Pat. No. 4,974,628 A, US 2009/104083 A1, DE 202006018959 U1, JP 2000283309 A, JP 2005133850 A, or JP 2006214539 A. A valve seat for high-pressure pumps, in particular, a valve seat for handling pressures exceeding 2,000 bar, is known from DE 3111614 A1.

DISCLOSURE

The problem addressed by the present invention is making available a valve for use in high-performance liquid chromatography that is particularly suitable for use at very high pressures. That problem is solved by a valve having those characteristics stated in the independent claim. Further beneficial embodiments thereof are stated in the dependent claims.

Under an embodiment of the invention, a valve for use in high-performance liquid chromatography has a spherical seat and a ball that, when it abuts against the spherical seat, constrains a fluid from flowing through the valve and is capable of moving axially in order to allow fluid to flow through the valve. The spherical seat has beveled outer faces in order that a force acting on the valve along the axial direction will generate a force acting on the ball. The inclinations of its beveled outer faces are such that the force acting on the ball counteracts a force exerted on the spherical seat by the ball and essentially compensates it, which allows accommodating a radial force exerted on the spherical seat by the ball and combats damage to, or destruction of, the spherical seat.

Under an embodiment, the force exerted on the ball has a radial component.

The force exerted on a sealing edge of the spherical seat by the ball may have a first planar force field and the force acting on the ball may have a second planar force field and is opposingly superimposed on the first force field and essentially compensates it.

The force exerted on the ball may exceed a force exerted on the spherical seat by the ball.

Under an embodiment, a restoring force that presses the ball against the spherical seat acts on the ball in order to constrain the fluid from flowing through the valve. That restoring force may be generated by a drop in system pressure across the ball, as well as by a spring, a weight, the ball's weight, an elastomer, etc.

The spherical seat and/or the ball may, preferably, consist of a ceramic, ruby, or sapphire material.

Under an embodiment, a first, beveled, outer face of the spherical seat abuts against a first housing component of the valve. A second, beveled, outer face of the spherical seat may, preferably, abut against a second housing component of the valve.

Under an embodiment, the normals to the surfaces of the beveled outer faces of the spherical seat are inclined relative to a direction, along which the fluid flows. Their inclinations may fall within the range 20°-70°, preferably within the range 30°-60°, and, more preferably, are about 45°.

A high-performance liquid-chromatography system according to the present invention has a pump for propelling a mobile phase, a stationary phase for separating components of a sample liquid brought into the mobile phase, and a valve, as stated above, that is situated in a flow path of the mobile phase. The high-performance liquid-chromatography system may also have a sample injector for bringing the sample liquid into the mobile phase, a detector for detecting separated components of the sample liquid, and/or a fractioning device for outputting the separated components of the sample liquid.

Embodiments of the present invention may be based on many of the known HPLC systems, such as the Agilent Infinity 1290, 1260, 1220, and 1200 series of the applicant, Agilent Technologies, Inc. Cf. www.agilent.com.

A pure solvent, or a mixture of various solvents, may be employed as the mobile phase, or eluent. The mobile phase may be chosen such that the retention times of the components of interest and/or the quantities of the mobile phase needed for pursuing chromatography will be minimized. The mobile phase may also be chosen such that certain components will be efficiently separated. The mobile phase may be an organic solvent, such as methanol or acetonitrile, which frequently will be diluted with water. Water and an organic solvent, or another solvent commonly employed in HPLC, are frequently employed when running in gradient mode, under which their mixing ratio is varied over time.

DESCRIPTION OF THE DRAWINGS

The invention will be explained in greater detail below by way of references to the drawings, where the same reference symbols refer to the same, or functionally equivalent or similar, characteristics.

In particular, FIG. 1 depicts a generalized representation of a liquid-separation system 10. A pump 20 receives a mobile phase from a solvent supply 25, typically via a degasser 27 that degasses the mobile phase and thereby reduces the quantities of dissolved gases present in the mobile phase. The pump 20 propels the mobile phase through a separation device 30, such as a chromatographic column, having a stationary phase. A sample device, or sample injector 40, may be provided between the pump 20 and the separation device 30 in order to allow bringing a sample fluid into the mobile phase. The stationary phase of the separation device 30 has been adapted to separating components of the sample fluid. A detector 50 detects the separated components of the sample fluid, and a fractioning device 60 may be provided for outputting the separated components.

The mobile phase may consist of a single solvent or a mixture of various solvents. Their admixing may be performed at a low pressure and ahead of the pump 20 in order that the pump 20 will propel the solvent mixture as the mobile phase. Alternatively, the pump may consist of discrete pumping units, where every pumping unit propels a single solvent, or solvent mixture, in order that the admixing of the mobile phase, as seen by the separation device 30, occurs under high pressure, and following the pump 20. The composition (mixing ratio) of the mobile phase may be either held constant over time (isocratic mode) or varied over time under what is termed "gradient mode."

A data-processing unit 70, which may be either a conventional PC or a workstation, may be interfaced to one or more devices on the liquid-separation system 10, as indicated by the arrows and dashed lines, in order to allow it to acquire data and/or operate the system or control individual components thereof.

Figure 1:
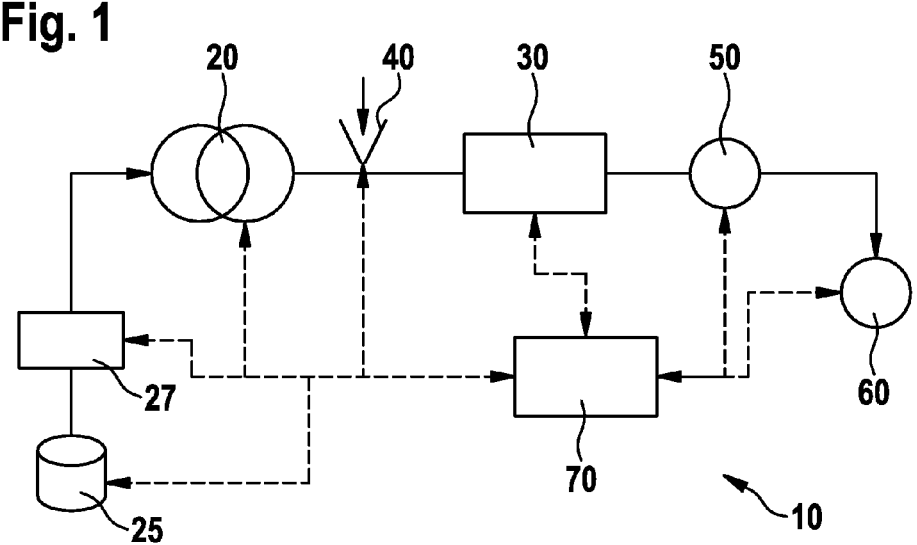
FIG. 1 depicts a liquid-separation system 10 corresponding to embodiments of the present invention, as employed in, e.g., HPLC.
Figure 2:
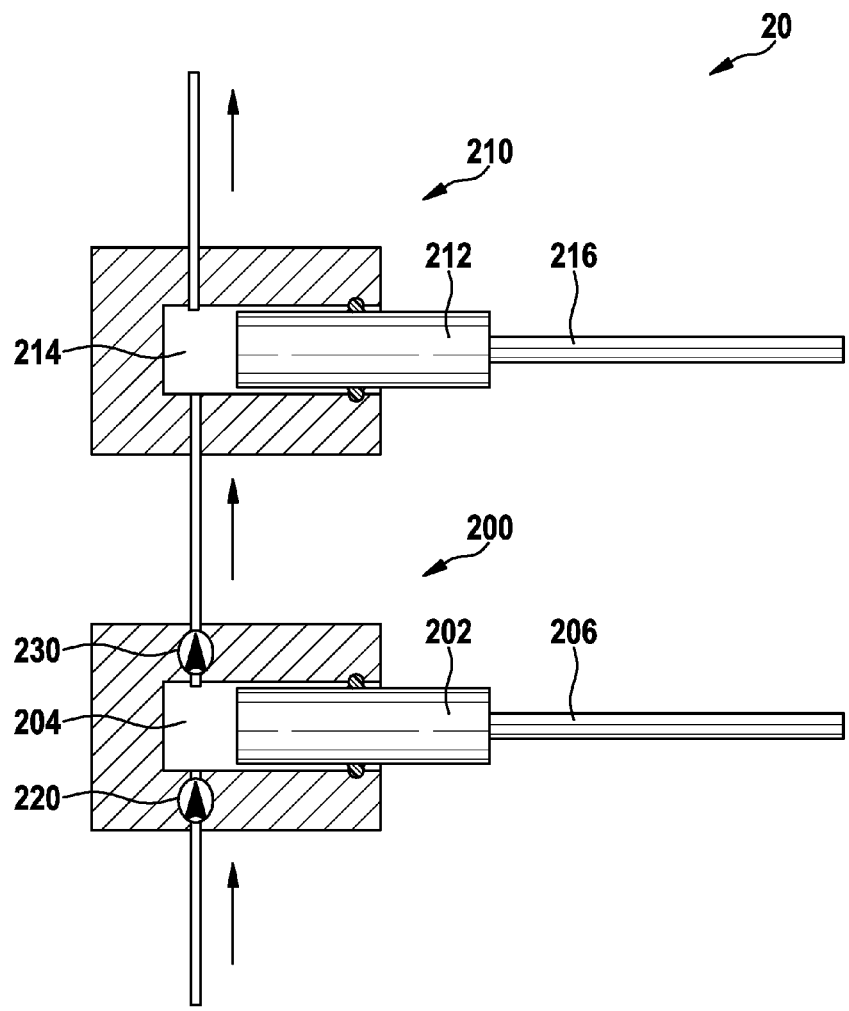
FIG. 2 depicts an embodiment of the pump 20.

FIG. 2 depicts an embodiment of the pump 20, as known from the aforementioned EP 0309596 A1. The pump 20 consists of a serial arrangement of a primary pump 200 and a secondary pump 210 in order to provide for continuous propulsion of liquid through the HPLC system 10. The primary pump 200 has a displacement piston 202 that may be moved back and forth in a cylinder 204 by a drive 206, schematically depicted in the form of a connecting rod, in order to induct and expel liquid. The secondary pump 210 also has a displacement piston 212 that may be moved back and forth in a cylinder 214 by a drive 216, schematically depicted in the form of a connection rod, in order to induct and expel liquid.

In the case of this embodiment, an inlet valve 220 is situated at the inlet to the pump 200, and an outlet valve 230 is situated at its outlet. These valves may be, and preferably are, configured in the form of passive check valves. The inlet valve 220 allows induction of liquid by the primary pump's piston 202, but prevents inducted liquid present in the cylinder 204 from being expelled through the valve 220 when it is displaced by the piston. The outlet valve 230 remains closed during an induction stroke by the primary pump's piston 202 and opens when the inducted liquid present in the cylinder 204 is expelled, once the system pressure, i.e., the pressure downstream from the valve 230, or, in other words, the pressure under which the liquid is propelled through the column 30, has been reached. Correspondingly, the outlet valve 230 between the primary pump 200 and the secondary pump 210 provides both that the primary pump 200 is unable to propel liquid into the system until the system pressure has been reached and that the secondary pump 210 propels liquid into the system, but not back into the primary pump 200. The outlet valve 230 may also be configured in the form of a redundant, dual-ball valve in order to improve system reliability.

Figure 3:
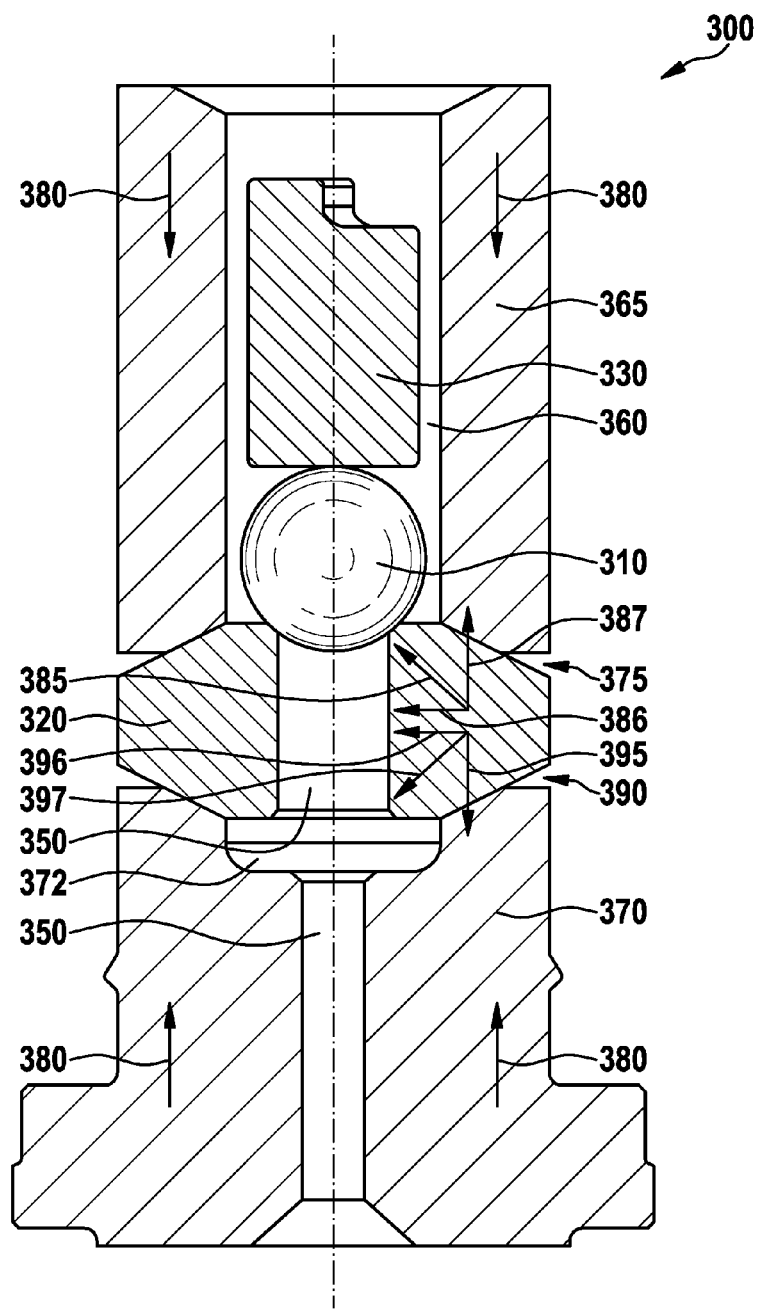
FIG. 3 depicts an embodiment of a valve 300 according to the invention.

FIG. 3 depicts a valve 300 according to an embodiment of the invention that might, for example, be situated at any location where the valves 220 and 230 shown in FIG. 2 might be situated. A ball 310 abuts against a spherical seat 320, where a restoring force 330 presses the ball 310 against the spherical seat 320 in order that the ball 310 will block a flow channel 350. The ball 310 will not open the flow channel 350 and allow liquid to flow past it and into the adjacent flow channel 360 until the pressure exerted on it by the liquid exceeds the pressure exerted on it by the restoring force 330.

The restoring force 330 schematically depicted in FIG. 3 represents both a drop in system pressure across the ball 310 and another force, such as a force exerted by a spring, as depicted in the aforementioned DE 202006018959 U1, a weight, the ball's weight, an elastomer, etc. A pushrod (not shown) that protrudes through the spherical seat 320 and lifts the ball 310, and, for example, might be actuated by a solenoid, may also be employed for opening the valve 300. Combinations of the aforementioned means might also be utilized for generating the restoring force 330.

The spherical seat 320 is surrounded by a first housing component 365 and a second housing component 370 and held in place by them. In the case of the example shown in FIG. 3, the ball 310 is encircled by the first housing component 365 and the latter encloses the flow channel 360, while the second housing component 370 encloses the flow channel 350. FIG. 3 also depicts an optional cavity 372 that can benefit flushability.

A first outer surface 390 of the spherical seat 320 abutting against the second housing component 370 is beveled in order that a force 380, portrayed in FIG. 3 in the form of upward and downward compressive forces, acting on the valve along the axial direction generates a force 385 acting on the ball 310 that has a radial component 386 and an axial component 387. The effects of the force 385 acting on the ball 310 will be described in detail below. In the case of the example shown in FIG. 3, the spherical seat 320 also has a second outer face 375 abutting against the first housing component 365 that has a bevel whose inclination is inverted with respect to that of the bevel on the first outer face 390.

The sides of the housing components 365 and 370 abutting against the outer faces 375 and 390 are, preferably, also beveled in order to provide for good contacts between their respective abutting surfaces. The degree of sealing action occurring between the spherical seat 320 and the housing components 365 and 370 may be adjusted by configuring their abutting surfaces. For example, sealing action may be increased by reducing the areas of their abutting surfaces, as indicated in FIG. 3. Coating the housing components 365 and 370 with materials, such as gold, PEEK, elastomers, etc., that benefit that sealing action, or choosing suitable elastic materials, may allow attaining suitably adjusted sealing actions.

The radial force components 386 and 396 counteract the radial forces exerted on the spherical seat 320 resulting from the ball 310 being pressed against the spherical seat 320 that might cause a radial deformation (enlargement) of the spherical seat, and thus decrease both the likelihood of leaks and risks that breakage of the spherical seat 320 might occur under peak loading by those radial forces. A single beveled outer face 390 or 375 will be sufficient to generate those radial force components.

The valve 300 shown in FIG. 3 may also be enclosed by an outer housing (not shown), against which, e.g., the housing components 365 and 370 and/or the spherical seat 320 may abut.

The inclination of the beveled outer face 390 of the spherical seat 320 is determined by the location of the sealing edge of the spherical seat 320 relative to the ball 310 and the direction of the vector representing the resultant of those forces exerted on the spherical seat 320 by the ball 310, as will be explained in detail in conjunction with FIG. 4.

Figure 4:
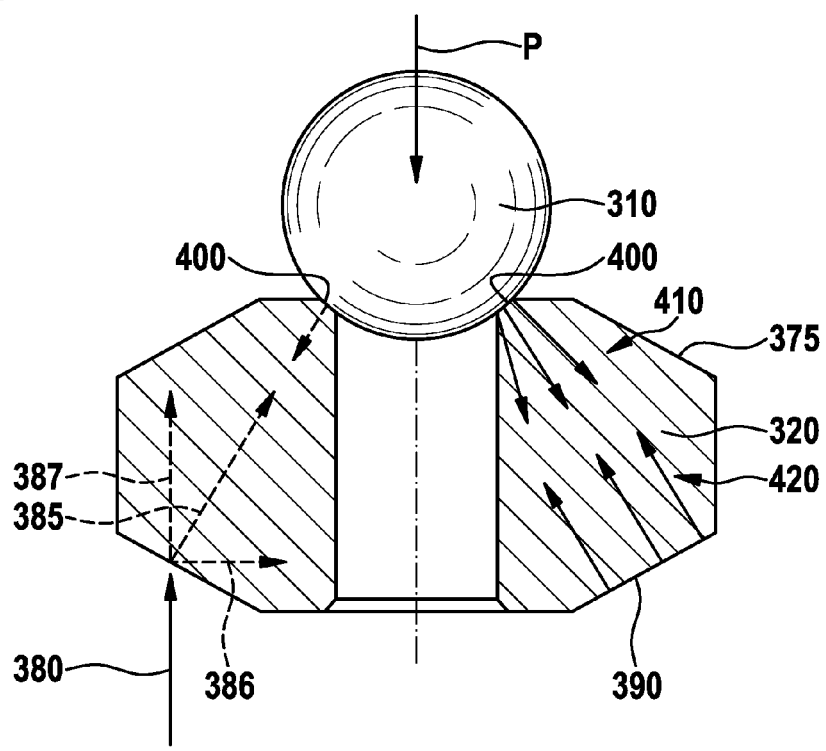
FIG. 4 schematically depicts the forces acting within the spherical seat 320.

FIG. 4 schematically depicts the forces acting within the spherical seat 320, where the relationships shown in FIG. 4 are referenced to the installed status shown in FIG. 3. The ball 310 is pressed into the spherical seat 320 by the system pressure, P, schematically represented by an arrow, acting within the mobile phase and abuts against a sealing edge 400. The sealing edge 400 represents the surface on the spherical seat 320 contacted by the ball 310 and yields a sealing action of the valve 300 whenever the ball 310 is pressed into the spherical seat 320. The sealing edge 400 is typically a ground-in, spherical surface. Pressing the ball 310 against the sealing edge 400 on the spherical seat 320 generates a planar force field 410. An oppositely directed force field 420 must be generated in order to prevent deformation of the spherical seat 320 by the force field 410. That force field 420 is due to the force 385, whose direction is determined by the inclination of the outer face 390, relative to the axial direction. The inclination of the outer face 390 should therefore be chosen such that the force fields 410 and 420 will ideally be oppositely superimposed on one another and thus compensate one another.

Due to the clamping action spread over the beveled surface 390, an oppositely directed force field 420 will be exerted on the ball 310 via the sealing edge 400 if the beveled surface's inclination has been correctly chosen. Suitable spatial configurations of the spherical seat 320, and, in particular, the outer face 390, in relation to the second housing component 370 will allow providing that the pair of force fields is essentially symmetrically superimposed on one another and thus yield a uniformly distributed compensation of the acting forces.

The force ratio, i.e., the ratio of the force fields 410 and 420, is duly chosen such that the clamping of the spherical seat 320 yields a greatly increased force 385 in order that the weaker force exerted on the sealing edge 400 by the ball 310 will be insufficient to cause deformation of the spherical seat 320 along the sealing edge 400. The dimensional stability of the spherical seat 320 will thus be maintained, even at peak force levels (peak pressure levels).

The designations "beveled" or "bevel" refer to an angling of the outer faces 375 and 390 relative to the axial direction such that the normals to their surfaces are inclined at included angles of less than 90° with respect to the axial-direction vector, represented by the arrow 380. In the case of the example shown in FIG. 3, the inclinations of their beveled surfaces are approximately 30°-60°, and preferably 40°. Obviously, their inclinations must be oriented such that the radial force components 386 and 396 are directed inward, i.e., toward the ball 310, as shown in FIG. 3. The inclinations of the outer faces 375 and 390 are thus inversely oriented, relative to one another.

In the case of a sample embodiment, the normal(s) to the beveled outer faces 375 and/or 390 of the spherical seat 320 are inclined relative to a flow direction of the fluid, where their inclination angle(s) may fall within the range 20°-70°, preferably within the range 30°-60°, and, more preferably, are about 45°.

The designations "axial" and "radial" refer to the sample embodiment of a cylindrical, essentially rotationally symmetric, valve 300 shown in FIG. 3. The same applies to other forms of the valve 300, such as rectangular embodiments, in which case, "axial" would essentially refer to the flow direction, or a direction opposite to the flow direction, and "radial" would refer to directions orthogonal thereto.

The spherical seat 320 and/or ball 310 may consist of a ceramic, ruby, or sapphire material, such as SiC, sintered SiC(SSiC), $Al_2O_3$, ZrO, or combinations thereof, where, e.g., either the entire spherical seat 320, or at least that portion thereof against which the ball 310 abuts, may be fabricated from the ceramic material. Under an embodiment, both the ball 310 and spherical seat 320, i.e., that zone of the stricture on which the ball acts, are typically fabricated from a ceramic material. The spherical seat 320 may also consist of a sapphire material and the ball 310 of a ruby material. Furthermore, the ball may be fabricated from a ruby material, while the spherical seat consists of a ceramic material. Those combinations of materials both allow employing very high pressures and have proven particularly suitable for use in conjunction with employment of a wide variety of solvents. Pressures of 1,000 bar and more may be employed without the spherical seat cracking. The other components of the valve may consist of known materials or combinations thereof, such as SST, PEEK, or PEEK constituents.

The invention claimed is:

1. A valve for use in high-performance chromatography, comprising;
   a spherical seating structure having a sealing surface, and
   a ball configured for constraining, when it abuts against the sealing surface of the spherical seating structure, a fluid from flowing through the valve and for moving in an axial direction in order to allow the fluid to flow through the valve,
   wherein the spherical seating structure has a beveled outer face separate and apart from the sealing surface, the beveled outer face being inclined with respect to the axial direction, cooperating with a housing structure and being configured such that a force acting on the valve along the axial direction generates a force acting on the ball, and
   wherein the inclination of the beveled outer face is configured such that the force acting on the ball counteracts a force exerted by the ball on the spherical seating structure and essentially compensates it.

2. The valve according to claim 1, wherein the force acting on the ball has a component along the radial direction.

3. The valve according to claim 1, wherein the force exerted by the ball on the sealing surface of the spherical seating structure is a first planar force field, and the force acting on the ball is a second planar force field and opposingly superimposed on the first force field and essentially compensates it.

4. The valve according to claim 1, wherein a restoring force acting on the ball is configured to press the ball against the sealing surface of the spherical seating structure in order to constrain the fluid from flowing through the valve.

5. The valve according to claim 4, wherein the restoring force acting on the ball is due to a spring, a weight, the weight of the ball, and/or an elastomer.

6. The valve according to claim 1, wherein at least one of the spherical seating structure and the ball comprises at least one of a ceramic, ruby, or sapphire material.

7. The valve according to claim 1, wherein the spherical seating structure includes a second beveled outer face abuts against a second housing component.

8. The valve according to claim 1, wherein the beveled outer face is inclined with respect to the axial direction by an inclination within a range of 20°-70°.

9. The valve according to claim 8, wherein the inclination is within a range of 30°-60°.

10. The valve according to claim 8, wherein the inclination is about 45°.

11. A high-performance liquid-chromatography system having a pump configured for moving a mobile phase, a stationary phase configured for separating components of a sample liquid comprised into the mobile phase, and a valve, according to claim 1 situated in a flow path of the mobile phase.

12. The high-performance liquid-chromatography system according to claim 11, comprising at least one of: a sample injector configured for injecting the sample liquid into the mobile phase; a detector configured for detecting separated components of the sample liquid; a fractioning device configured for outputting separated components of the sample liquid.

* * * * *